United States Patent
Kobayashi et al.

(10) Patent No.: US 6,235,921 B1
(45) Date of Patent: *May 22, 2001

(54) AMINES OR SALTS THEREOF AND METHODS OF PREPARING SAME

(75) Inventors: Hiroshi Kobayashi, Chikushino; Jin Nie, Kasuga; Takaaki Sonoda, Fukuoka, all of (JP)

(73) Assignee: Central Glass Company, Limited, Ube (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/579,619

(22) Filed: Feb. 12, 1996

(30) Foreign Application Priority Data

Feb. 13, 1995 (JP) .................................................. 7-024301

(51) Int. Cl.$^7$ .................................................. C07C 303/00
(52) U.S. Cl. .................................................. 558/47
(58) Field of Search .................................................. 558/47

(56) References Cited

U.S. PATENT DOCUMENTS 5,258,066 * 11/1993 Kobayashi et al. ..................... 106/22
5,387,700 * 2/1995 Maryanoff et al. .................. 549/387
5,414,120 * 5/1995 Pohmer et al. ......................... 564/82
5,502,251 * 3/1996 Pohmer et al. ......................... 564/82

FOREIGN PATENT DOCUMENTS

2239817 * 2/1974 (DE) .
7-246338   9/1995 (JP) .

OTHER PUBLICATIONS

Argyropoulos et al., "Condensation Products from Imidobis-(sulfurylchloride)." J. of Applied Polymer Science, vol. 26, pp. 3073–3084, 1981.*
Hauptschein et al., Fluorocarbon Halosulfates and a New Route to Fluorocarbon Acids and Derivatives, *Journal of American Chemical Society*, vol. 83, 2505–2507 (1961).
Foropoulos et al., Synthesis, Properties, and Reactions of Bis((trifluoromethyl)sulfonyl)Imide, *Inorganic Chemistry*, vol. 23, No. 23, 3720–23 (1984).
Argyropoulos et al., –"Journal of Applied Polymer Science", vol. 26, 3073–3084 (1981).
"Inorganic syntheses", vol. VIII, 1966, pp. 105–107.

* cited by examiner

Primary Examiner—Barbara P. Badio
(74) Attorney, Agent, or Firm—Evenson, McKeown, Edwards & Lenahan, P.L.L.C.

(57) ABSTRACT

The invention relates to a process for the preparation of $M[Rf^1OSO_2NSO_2ORf^2]_n$ wherein $Rf^1$ and $Rf^2$ are as define any the specification by reacting bis(chlorosulfonyl)amine with a fluoroalcohol represented $Rf^3OH$ wherein $Rf^3$ represents the same of different group which is identical with $Rf^1$ and $Rf^2$.

9 Claims, No Drawings

AMINES OR SALTS THEREOF AND METHODS OF PREPARING SAME

BACKGROUND OF THE INVENTION

The present invention relates to amines or salts thereof, which are useful as catalyst and the like, and to methods of preparing the amines or the salts.

Of amines, for example, metal salts of sulfonylamines and hydrates of these salts are disclosed in Japanese Patent Unexamined Publication JP-A-Hei-7-246338. These compounds disclosed therein are usable as Lewis acid catalysts and represented by the following general formula of $M[RfSO_2-N-SO_2Rf']_n$ or of $M[RfSO_2-N-SO_2Rf']_n \cdot mH_2O$ wherein Rf and Rf' each represent perfluoroalkyl groups having a carbon atom number from 1 to 8, M represents a positive ion selected from a special group disclosed therein, n represents an integer that is the same as the valence of M, and m represents a natural number from 0.5 to 20.

Argyropoulos et al. Journal of Applied Polymer Science, Vol. 26, 3073–3084 (1981) discloses, as another example of amines, bis(ethoxysulfonyl)amine, $HN(C_2H_5OSO_2)_2$, and polysulfonylamine.

SUMMARY OF THE INVENTION

It is an object of the present invention to provide a novel amine or its salt, which has a fluorocarbon sulfonic acid ester group, and a method of preparing the amine or its salt.

According to the present invention, there is provided a novel first compound which is one of a first amine and a first salt of the first amine. This first compound has a fluorocarbon sulfonic acid ester group, and is represented by the general formula (1) (thus hereinafter referred to as "the first compound (1)", "the first amine (1)", or "the first salt (1)"):

$$M[Rf^1OSO_2NSO_2ORf^2]_n \qquad (1)$$

wherein $Rf^1$ and $Rf^2$ represent the same or different fluorine-containing monovalent organic groups each of which has a carbon atom number from 2 to 18, a straight-chain portion, a branched-chain portion and/or a ring chain portion, and an optional unsaturated bond and an optional oxygen atom; M represents a positive ion which has a first valence and is one selected from the group consisting of hydrogen ion, ammonium ion, quaternary ammonium ions, alkali metal ions, alkali earth metal ions, transition metal ions, rare earth element ions, aluminum ions, gallium ions, iridium ions, thallium ions, tin ions, lead ions, arsenic ions, antimony ions, and bismuth ions; and n represents an integer that is the same as the first valence.

According to the present invention, there is provided a first method of preparing the first compound (1). This first method comprises the step of:

(a) reacting bis(chlorosulfonyl)amine represented by the formula (2) (hereinafter referred to as "the bis(chlorosulfonyl)amine (2)") with a fluoroalcohol represented by the general formula (3) (hereinafter referred to as "the fluoroalcohol (3)"), so as to prepare the first amine (1) wherein M represents a hydrogen ion, and n is 1,

$$HN(SO_2Cl)2 \qquad (2)$$

$$Rf^3OH \qquad (3)$$

wherein $Rf^3$ represents the same or different groups which are identical with the $Rf^1$ and the $Rf^2$.

According to the present invention, there is provided a novel second compound which is one of a second amine and a second salt of the second amine. This second compound has a fluorocarbon sulfonic acid ester group, and is represented by the general formula (4) (thus hereinafter referred to as "the second compound (4)", "the second amine (4)", or "the second salt (4)"):

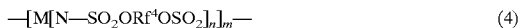

$$-[M[N-SO_2ORf^4OSO_2]_n]_m- \qquad (4)$$

wherein $Rf^4$ represents a fluorine-containing bivalent organic group which has a carbon atom number from 3 to 18, a straight-chain portion, a branched-chain portion and/or a ring chain portion, and an optional unsaturated bond and an optional oxygen atom; M represents a positive ion as defined above; n represents an integer as defined above, and m represents an integer from 1 to 1,000.

According to the present invention, there is provided a second method of preparing the second compound (4). The second method comprises the step of:

(b) reacting bis(chlorosulfonyl)amine (2) with a fluorodiol represented by the general formula (5) (hereinafter referred to as "the fluorodiol (5)"), so as to prepare the second amine (4) wherein M is a hydrogen ion, and n is 1,

$$HORf^5OH \qquad (5)$$

wherein $Rf^5$ represents a bivalent organic group which is identical with $Rf^4$.

In the invention, the above-mentioned first method further optionally comprises, after the step (a), the step of: (c) reacting the first amine (1) with a third compound, so as to prepare the first salt (1), the third compound being one selected from the group consisting of ammonia, quaternary ammonium compounds, hydroxides of an element, oxides of the element, carbonates of the element, halides of the element, fluorides of the element, chlorides of the element, bromides of the element, iodides of the element, and acetates of the element, the element being one selected from the group consisting of alkali metals, alkali earth metals, transition metals, rare earth elements, aluminum, gallium, iridium, thallium, tin, lead, arsenic, antimony, and bismuth.

In the invention, the above-mentioned second method further optionally comprises, after the step (b), the step of: (d) reacting the second amine (4) with the above-mentioned third compound, so as to prepare the second salt (4).

Similar to the above-mentioned conventional metal salts of sulfonylamines and hydrates of these metal salts, the first and second compounds (1) and (4) according to the present invention have fluorine-containing amine ions. These amine ions are stabilized by a strong electron attractive force of the fluorine atoms. Thus, the ionic bond between the fluorine-containing amine ions and the positive ions becomes small. With this, the first and second compounds (1) and (4) have large dissociation constants. Therefore, these compounds (1) and (4) are fully expected to be usable as a catalyst and the like, in the synthesis of organic compounds.

DESCRIPTION OF THE PREFERRED EMBODIMENTS

A novel first compound (1) according to the present invention is represented by the general formula (1):

$$M[Rf^1OSO_2NSO_2ORf^2]_n \qquad (1)$$

wherein $Rf^1$ and $Rf^2$ represent the same or different fluorine-containing monovalent organic groups. Examples of these groups are fluorine-containing straight chain or branched chain alkyl and alkenyl groups each having a carbon atom number from 2 to 18, fluorine-containing cycloalkyl and cycloalkenyl groups each having a carbon atom number from 3 to 18, fluorine-containing aryl groups each having a carbon atom number from 6 to 18, and mixtures thereof. Preferable examples of $Rf^1$ and $Rf^2$ are fluoroalkyl groups represented by $RfCH_2$— and $(Rf)_2CH$— where Rf is a fluoroalkyl group having a carbon atom number from 1 to 8.

Preferable examples of the positive ion represented by M in the general formula (1) are hydrogen ion, ammonium ion, quaternary ammonium ions, alkali metal ions, alkali earth metal ions, transition metal ions, and rare earth element ions.

The first compound (1) has the following six exemplary structures.

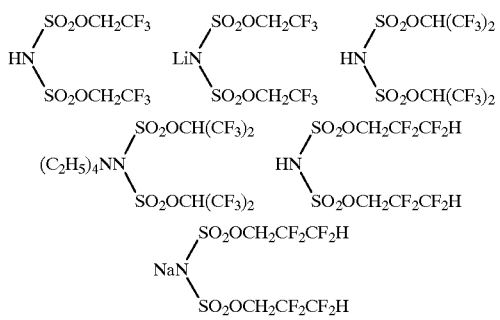

The above-mentioned bis(chlorosulfonyl)amine (2) used for preparing the first amine (1) can be synthesized, for example, by a method disclosed in Inorganic Syntheses, Vol. VIII, 1966, pp. 105–107, using phosphorus(V) chloride, sulfonic acid amide, and chlorosulfonic acid.

Preferable examples of the above-mentioned fluoroalcohol (3) used for preparing the first amine (1) are $RfCH_2OH$ and $(Rf)_2CHOH$ where Rf represents a fluoroalkyl group having a carbon atom number from 1 to 8, such as 2,2,2-trifluoroethylalcohol ($CF_3CH_2OH$), 2,2,3,3,3-pentafluoropropanol ($CF_3CF_2CH_2OH$), 1,1,1,3,3,3-hexafluoro-2-propanol (($CF_3)_2CHOH$), and 2,2,3,3-tetrafluoropropanol ($CF_2HCF_2CH_2OH$).

In the step (a) of the above-mentioned first method, bis(chlorosulfonyl)amine (2) is reacted with the fluoroalcohol (3), in a solvent or without using solvent, for preparing the first amine (1). In order to obtain a higher yield, it is preferable to react 1 part by mol of bis(chlorosulfonyl)amine (2) with 2 parts by mol of the fluoroalcohol (3). This reaction is expressed as the following reaction formula (1).

$$HN(SO_2Cl)_2 + 2Rf^3OH \rightarrow HN(SO_2ORf^3)_2 + 2HCl \qquad (1)$$

In the step (a), $Rf^1$ and $Rf^2$ of the first amine (1) become different groups by at first reacting one type of the fluoroalcohol (3) with an excessive amount of the bis(chlorosulfonyl)amine (2) so as to produce $HN(SO_2ORf^3)(SO_2Cl)$, and then by reacting this product with another type of the fluoroalcohol (3).

The step (a) is conducted preferably at a temperature within a range from about 0° C. to about 200° C. and more preferably at a temperature within a range from 40° C. to 100° C. If it is lower than about 0° C., the reaction rate becomes substantially slow. If it is higher than about 200° C., the raw materials of the reaction, the solvent if used, and the reaction product may be decomposed.

In the step (a), it is possible to use a solvent not limited to a particular type, as long as it is inert in the reaction. Examples of this solvent are halogenated hydrocarbons such as methylene chloride, ethylene chloride and perfluorocarbons; hydrocarbons such as benzene, heptane and cyclohexane; ethers such as diethyl ether, diisopropyl ether and dioxane; and nitriles such as acetonitrile.

In the step (a), the reaction product (i.e., the first amine (1)) can be obtained as a fluoroalkoxy-sulfonylamine by removing the solvent after the reaction, through evaporation or distillation. The thus obtained reaction product can be purified through sublimation under reduced pressure or through recrystallization.

For example, the first salt (1), that is, the ammonium salt of the first amine (1), is obtained in the above-mentioned step (c) of the first method, when the first amine (1) is reacted with ammonia (i.e., the third compound). Furthermore, the first salt (1), that is, the quaternary ammonium salt of the first amine (1), is obtained in the step (c), when the first amine (1) is reacted with a substitution compound of ammonia. Examples of this substitution compound are primary, secondary and tertiary amines such as methylamine, diethylamine and triethylamine, heterocyclic amines such as pyridine and piperidine, aromatic amines such as aniline, quaternary ammonium halides such as tetraethylammonium fluoride, and quaternary ammonium hydroxides such as tetraethylammonium hydroxide. Still furthermore, the first salt (1) other than the above-mentioned types is obtained in the step (c), when the first amine (1) is reacted with a hydroxide of an element, an oxide of this element, a carbonate of this element, halides of this element, fluorides of this element, chlorides of this element, bromides of this element, iodides of this element, or an acetate of this element. This element is one selected from the group consisting of alkali metals (e.g., lithium, sodium and potassium), alkali earth metals (e.g., magnesium and calcium), transition metals (e.g., titanium, vanadium, manganese, cobalt, nickel, copper, silver, zinc and cadmium), rare earth elements (e.g., lanthanum), aluminum, gallium, iridium, thallium, tin, lead, arsenic, antimony, and bismuth.

As is mentioned above, the second compound (4), an fluoroalkoxysulfonylamine polymer, is represented by the general formula (4):

$$-[M\,[N-SO_2ORf^4OSO_2]_n]_m- \qquad (4)$$

wherein $Rf^4$ represents a fluorine-containing bivalent organic group. Examples of this group are fluorine-containing straight chain or branched chain alkylene and alkenylene groups each having a carbon atom number from 3 to 18, fluorine-containing cycloalkylene and cycloalkenylene groups each having a carbon atom number from 3 to 18, fluorine-containing arylene groups each having a carbon atom number from 6 to 18, and mixtures thereof. Preferable examples of $Rf^4$ are fluoroalkylene groups represented by —$CH_2RfCH_2$— where Rf is a fluoroalkylene group having a carbon atom number from 1 to 8. Examples of the second compound (4) are polymeric [(polyfluoroalkoxy)sulfonyl]amine, —[$CHN-SO_2OCH_2(CF_2)_4CH_2OSO_2]_m$—, and lithium salt of polymeric [(polyfluoroalkoxy)sulfonyl]amine, —[$LiN-SO_2OCH_2(CF_2)_4CH_2OSO_2]_m$—.

In the step (b) of the above-mentioned second method, bis(chlorosulfonyl)amine (2) is reacted with the fluorodiol (5), in a solvent or without using solvent, so as to prepare the second amine (4). Carbon atom(s) in the group of $Rf^5$ in the general formula (5), each of the carbon atom(s) is directly bonded to oxygen atom, is preferably not directly bonded to fluorine atom(s). An example of the fluorodiol (5) is $HOCH_2(CF_2)_nCH_2OH$ where n is an integer from 1 to 8.

The molecular weight of the second amine (4) can be controlled by adjusting the reaction condition of the step (b). In other words, it can be controlled, for example, by adjusting the reaction temperature, or by selecting a suitable solvent among solvents different in polarity. The reaction in the step (b) is expressed as the following reaction formula (2).

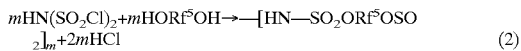
(2)

The step (b) is conducted preferably at a temperature within a range from about 10° C. to about 200° C. If it is lower than about 0° C., the reaction rate becomes substantially slow. If it is higher than about 200° C., the raw materials of the reaction, the solvent if used, and the reaction product may be decomposed.

In the step (b), it is possible to use a solvent not limited to a particular type, as long as it is inert in the reaction. Examples of this solvent are the same as those of the solvent usable in the step (a).

In the step (b), the reaction product (i.e., the second amine (2)) can be obtained as an fluoroalkoxy-sulfonylamine polymer, by filtering precipitate out of the reaction solution, and then by removing the solvent from the precipitate through evaporation or distillation.

Similar to the step (c), the second salt (4) of the second amine (4) is obtained in the above-mentioned step (d) of the second method, when the second amine (4) is reacted with ammonia, the above-mentioned quaternary ammonium compound, a hydroxide of the above-mentioned element, an oxide of the element, a carbonate of the element, a halide of the element, a fluoride of the element, a chloride of the element, a bromide of the element, an iodide of the element, or an acetate of the element.

The following examples are illustrative of the present invention, but these examples are not limitative.

EXAMPLE 1

(A) PREPARATION OF BIS (CHLOROSULFONYL)AMINE

A raw material for preparing the first amine (1), that is, bis(chlorosulfonyl)amine (2), was prepared as follows. At first, 19.4 g of sulfonic acid amide and 83.4 g of phosphorus (V) chloride were introduced into a 200-ml flask equipped with a reflux condenser and with a tube charged with an anhydrous calcium chloride desiccating agent. This mixture was heated to 100° C. and stirred for 5 hr until the termination of the HCl gas generation. The reaction mixture was distilled under a pressure of 20 mmHg at 80° C., thereby removing a by-product of $POCl_3$. The thus obtained reaction product was reacted with 26.5 g of chlorosulfonic acid under a reduced pressure of 15 mmHg at 80° C. for 8 hr. Then, the unreacted chlorosulfonic acid was distilled out under 10 mmHg at 100° C. The thus obtained reaction product was distilled two times under 1 mmHg, thereby obtaining 34.5 g of bis(chlorosulfonyl) amine.

(B) PREPARATION OF BIS[(2,2,2-TRIFLUOROETHOXY)SULFONYL]AMINE

The first amine (1) was prepared by the step (a) of the first method as follows. At first, 2.415 g of the above-prepared bis(chlorosulfonyl)amine and 20 ml of dried benzene were introduced into a flask equipped with a reflux condenser and with a tube charged with an anhydrous calcium chloride desiccating agent. Then, 2.253 g of 2,2,2-trifluoroethanol, $CF_3CH_2OH$, was added dropwise to this mixture, while this mixture was stirred. The reaction mixture was heated under reflux condition. After the HCl generation decreased, the reaction mixture was maintained under the same heated condition for 1 hr. Then, benzene used as a solvent was evaporated, thereby leaving 3.70 g of a highly-viscous solid matter. Then, this solid matter was sublimed under 0.2 mmHg at 80° C., and then was trapped by cooling with ice. With this, 3.48 g of white crystals was obtained. This final product was identified as bis[(2,2,2-trifluoroethoxy) sulfonyl]amine, $HN(SO_2OCH_2CF_3)_2$. The yield was 94%. The following are the obtained characteristics and identification data of this final product (i.e., melting point, NMR data, infrared spectrum data, mass spectrum data, and elemental analysis data).

Melting Point: 55–58° C.

$^1$H-NMR (Solvent: $CD_3CN$, Internal Standard: TMS):
    4.79 (q,4H, $CH_2$,$^2$J(F-H)=8 Hz) 8.09 (B, 1H, H-N)

$^{19}$F-NMR (Solvent: $CD_3CN$, Internal Standard: $C_6F_6$)
    89.1 (t,6F,$CF^3$,$^2$J(H-F)=8 Hz)

Infrared Spectrum ($CCl_4$ solvent, $cm^{-1}$):
    3342(w),1550(s),1439(m),1334(w),1286(m)
    1252(m),1212(m),1180(s),1141(w),1105(w)
    1046(m),1007(m),978(m),769(vs)

Mass Spectrum (m/z):
    341($M^{+,}$1),322(14),272(38),242(100),
    222(17),192(31),163(31),79(47)

Elemental Analysis:
    (Calculated Values: C 14.09; H 1.48; N 4.11, F 33.41)
    Measured Values: C 14.19; H 1.65; N 4.07, F 33.81

EXAMPLE 2

In this example, the first salt (1) was prepared by the step (b) of the first method as follows. At first, 6.10 g of bis[(2,2,2-trifluoroethoxy)sulfonyl]amine prepared as in Example 1 was dissolved in 20 ml of water. Then, 0.661 g of lithium carbonate having a purity of 99.999% was added to this solution. Then, the reaction solution was stirred to generate carbon dioxide gas, and this solution was heated to 100° C. Then, the obtained precipitate was separated from the solution by filtration. Then, water was evaporated from the precipitate. The thus obtained solid matter was dried under 0.4 mmHg at 100° C. With this, 6.026 g of lithium salt of bis[(2,2,2-trifluoroethoxy)sulfonyl]amine, LiN($SO_2OCH_2CF3$)2, was obtained in the form of white powder. The yield was 97%.

EXAMPLE 3

In this example, Example 1 was slightly modified as follows. At first, 2.747 g of bis(chlorosulfonyl)amine prepared as in Example 1 and 20 ml of dried benzene were introduced into a flask which is the same as that of Example 1. Then, 3.852 g of 2,2,3,3,3-pentafluoro-propanol, $CF_3CF_2CH_2OH$, was added dropwise to this mixture, while this mixture was stirred. The reaction mixture was heated under reflux condition. After the HCl generation decreased, the reaction mixture was maintained under the same heated condition for 1 hr. Then, benzene used as a solvent was evaporated, thereby leaving 5.67 g of a highly-viscous solid matter. Then, this solid matter was sublimed under 0.15 mmHg at 90° C., and then was trapped by cooling with ice. With this, 5.110 g of white crystals was obtained. This final product was identified as bis[(2,2,3,3,3-pentafluoropoxy) sulfonyl]amine, $HN(SO_2OCH_2CF_2CF_3)_2$. The yield was 91%. The following are the obtained characteristics and identification data of the final product.

Melting Point: 58–59° C.

$^1$H-NMR (Solvent: CD$_3$CN, Internal Standard: TMS):
    4.86 (q,4H,CH$_2$ $^2$J(F-H)=12 Hz $^3$J(F-H)=0.97 Hz)
    8.02 (B, 1H, H-N)

$^{19}$F-NMR (Solvent: CD$_3$CN, Internal Standard: C$_6$F$_6$)
    40.43 (t,4F,$^1$J=12 Hz) 80.22(S,6F)

Infrared Spectrum (CCl4 solvent, cm$^{-1}$):
    3336(w),1550(s) ,1440(m),1351(w),1302(w)
    1256(m) ,1212(m) ,1159(m) ,1111(m) ,1039 (w)
    1011(s),979(m), 871(m), 769 (vs)

Mass Spectrum (m/z):
    441(M$^+$, 8),421(4),322(43),292(100),242(20),
    213(16),80(7),69(6)

Elemental Analysis:
    (Calculated Values: C 16.34; H 1.14; N 3.17, F 43.06)
    Measured Values: C 15.93; H 1.10; N 3.39, F 43.52

EXAMPLE 4

In this example, Example 2 was slightly modified as follows. At first, 4.416 g of bis[(2,2,3,3,3-pentafluoropropoxy)sulfonyl]amine obtained in Example 3 was dissolved in 20 ml of water. Then, 0.3699 g of lithium carbonate having a purity of 99.999% was added to this solution. Then, the reaction solution was stirred to generate carbon dioxide gas, and this solution was heated to 100° C. Then, the obtained precipitate was separated from the solution by filtration. Then, water was evaporated from the precipitate. The thus obtained solid matter was dried under 0.05 mmHg at 100° C. With this, 4.100 g of lithium salt of bis[(2,2,3,3,3-pentafluoro-propoxy)sulfonyl]amine, LiN(SO$_2$OCH$_2$CF$_2$CF$_3$)$_2$, was obtained in the form of white powder. The yield was 92%.

EXAMPLE 5

In this example, Example 1 was slightly modified as follows. At first, 2.550 g of bis(chlorosulfonyl)amine prepared as in Example 1 was introduced into a flask which is the same as that of Example 1. Then, 20 ml of 1,1,1,3,3,3-hexafluoro-2-propanol, (CF$_3$)$_2$CHOH, was added dropwise to the flask. The reaction mixture was heated under reflux condition, thereby conducting the reaction for 43 hr. After the HCl generation decreased, the reaction mixture was maintained under the same heated condition for 1 hr. Then, an excessive amount of alcohol was evaporated from the reaction mixture, thereby leaving 5.670 g of a highly-viscous solid matter. Then, this solid matter was sublimed under 0.25 mmHg at 80° C., and then was trapped by cooling with ice. With this, 5.358 g of white crystals was obtained. This final product was identified as bis[(1,1,1,3,3,3-hexafluoro-2-propoxy) sulfonyl]amine, HN(SO$_2$OCH(CF$_3$)$_2$)$_2$. The yield was 94%. The following are the obtained characteristics and identification data of the final product.

Melting Point: 92–94° C.

$^1$H-NMR (Solvent: CDCl$_3$, Internal Standard: TMS):
    5.34 (hepta,CH,$^2$J(F-H)=5 Hz)
    6.45 (s,H-N)

$^{19}$F-NMR (Solvent: CDCl$_3$, Internal Standard: C$_6$F$_6$)
    89.11 (d,CF$_3$,$^2$J(F-H)=7 Hz)

$^{13}$C-NMR (Solvent: CDCl$_3$, Internal Standard: C$_6$F$_6$)
    75.36 (hepta,C-H,$^2$J(F-C)=37 Hz)
    119.38 (q,CF$_3$, $^1$J(F-C)=283 Hz)

Infrared Spectrum (CCl$_4$ solvent, cm$^{-1}$):
    3336(w),1550(s),1461(m),1365(m),1302(w)
    1294(m),1243(s),1213(s),1114(m),1069(m)
    1005(s),769(vs)

Mass Spectrum (m/z):
    477(M$^+$, 40),458(30),408(100),309(4),231(40), 270(13),69(54)

Elemental Analysis:
    (Calculated Values: C 15.10; H 0.63; N 2.93, F 47.78)
    Measured Values: C 15.25; H 0.49; N 3.24, F 47.74

EXAMPLE 6

In this example, Example 2 was slightly modified as follows. At first, 1.250 g of bis[(1,1,1,3,3,3-hexafluoro-2-propoxy)sulfonyl]amine obtained in Example 5 was dissolved in 15 ml of acetonitrile. Then, 0.0968 g of lithium carbonate having a purity of 99.999% was added to this solution. Then, the reaction solution was stirred to generate carbon dioxide gas, and this solution was heated to 100 ° C. Then, the obtained precipitate was separated from the solution by filtration. Then, the solvent was evaporated from the precipitate. The thus obtained solid matter was dried under 0.05 mmHg at 100 ° C. With this, 1.00 g of lithium salt of bis[(1,1,1,3,3,3-hexafluoro-2-propoxy)sulfonyl]amine, LiN(SO$_2$OCH(CF3)$_2$)$_2$, was obtained in the form of white powder. The yield was 79%.

EXAMPLE 7

In this example, Example 1 was slightly modified as follows. At first, 2.880 g of bis(chlorosulfonyl)amine prepared as in Example 1 and 20 ml of dried benzene were introduced into a flask which is the same as that of Example 1. Then, 3.556 g of 2,2,3,3-tetrafluoropropanol, CF$_2$HCF$_2$CH$_2$OH, was added dropwise to this mixture, while this mixture was stirred. The reaction mixture was heated under reflux condition. After the HCl generation decreased, the reaction mixture was maintained under the same heated condition for 1 hr. Then, benzene used as a solvent was evaporated, thereby leaving 5.99 g of a highly-viscous solid matter. Then, this solid matter was sublimed under 0.05 mmHg at 120 ° C., and then was trapped at −90° C. With this, 5.260 g of white crystals was obtained. This final product was identified as bis[(2,2,3,3-tetrafluoropropoxy)sulfonyl]amine, HN(SO$_2$OCH$_2$CF$_2$CF$_2$H)$_2$. The yield was 96%. The following are the obtained characteristics and identification data of the final product.

Melting Point: 53–56° C.

$^1$H-NMR (Solvent: CD$_3$CN, Internal Standard: TMS):
    4.75 (t,4H,CH$_2$ $^2$J(F-H)=13 Hz, $^3$J(F-H)=1.5 Hz)
    6.19 (t,2H,CF$_2$H $^1$J(F-H)=52 Hz, $^2$J(F-H)=4 Hz)
    8.27 (s,1H,H-N)

$^{19}$F-NMR (Solvent: CD$_3$CN, Internal Standard: C$_6$F$_6$)
    25.15(d,4F,CF$_2$, $^1$J(H-F)=52 Hz $^2$J(F-F)=4 Hz)
    38.81(m,CF$_2$,4F)

Infrared Spectrum (CCl$_4$ solvent, cm$^{-1}$):
    3342(w),1947(w),1717(w),1550(s),1437(w)
    1375(w) ,1251(m) ,1214(s),1113(w) ,1005(m)
    979(m),819(s),769(s),754(vs)

Mass Spectrum (m/z):
    406(M$^+$+1,7),385(13),304(89),273(63)
    225(6),195(76),175(35),113(38),50(100)

Elemental Analysis:
    (Calculated Values: C 17.79; H 1.74; N 3.46, F 37.51)
    Measured Values: C 17.70; H 1.97; N 3.34, F 36.34

EXAMPLE 8

In this example, Example 2 was slightly modified as follows. At first, 4.194 g of bis[(2,2,3,3-tetrafluoro-propoxy)sulfonyl]amine obtained in Example 7 was dissolved in 20 ml of water. Then, 0.3824 g of lithium carbonate having a purity of 99.999% was added to this solution. Then, the reaction solution was stirred to generate carbon dioxide gas, and this solution was heated to 100° C. Then, the obtained precipitate was separated from the solution by filtration. Then, water was evaporated from the precipitate. The thus obtained solid matter was dried under 0.05 mmHg at 100° C. With this, 3.860 g of lithium salt of bis[(2,2,3,3-tetrafluoropropoxy)sulfonyl]amine, LiN(SO$_2$OCH$_2$CF$_2$CF$_2$H)$_2$, was obtained in the form of white powder. The yield was 91%.

EXAMPLE 9

In this example, Example 1 was slightly modified as follows. At first, 2.573 g of 2,2,3,3,4,4,5,5-octafluoro-1,6-hexanediol and 20 ml of dried benzene were introduced into a flask which is the same as that of Example 1. Then, a benzene solution in which 2.102 g of bis(chlorosulfonyl)amine had been dissolved was added dropwise to this mixture, while this mixture was stirred. The reaction mixture was heated under reflux condition. After the HCl generation decreased, the reaction mixture was maintained under the same heated condition for 5 hr. Then, the obtained precipitate was separated from the solution by filtration. The remaining solvent was evaporated from the precipitate. With this, 3.262 g of polymeric[(polyfluoroalkoxy)sulfonyl]amine, —[HN—SO$_2$OCH$_2$(CF$_2$)$_4$CH$_2$OSO$_2$]$_m$—, was obtained. The yield was 82%. The following are the obtained characteristics and identification data of the final product.
Melting Point: 131–133° C.
$^1$H-NMR (Solvent: CD$_3$CN, Internal Standard: TMS):
    4.02 (t,small)
    4.90 (t,big)
    8.68 (s,H-N)
$^{19}$F-NMR (Solvent: CD$_3$CN, Internal Standard: C$_6$F$_6$)
    41.79(t,small)
    44.34 (t,big)
Infrared Spectrum (CCl$_4$ solvent, cm$^{-1}$):
    3470(s water),2967(m),1628(m),1454(m),1343(s) 1163(s),1044(s),957(m),843(s),584(s)
Molecular Weight measured by GPC with polystyrene standard:
    Weight Average Molecular Weight (Mw)=4,300
    Number Average Molecular Weight (Mn)=3,400
Elemental Analysis:
    (Calculated Values: C 18.46; H 1.31; N 3.26, F 37.15)
    Measured Values: C 18.14; H 1.44; N 3.30, F 37.39

EXAMPLE 10

At first, 1.300 g of polymeric[(polyfluoroalkoxy)sulfonyl]amine obtained in Example 9 was reacted with 0.120 g of lithium carbonate in acetonitrile. Then, this solvent was distilled off. The thus obtained solid matter was dried under reduced pressure, thereby obtaining 1.300 g of lithium salt of polymeric[(polyfluoroalkoxy)sulfonyl]amine, —[LiN—SO$_2$OCH$_2$(CF$_2$)$_4$CH$_2$OSO$_2$]$_m$—. The yield was 98%.

EXAMPLE 11

In this example, 2.540 g of bis[(2,2,2-trifluoroethoxy)sulfonyl]amine obtained in Example 1 was reacted with 1.026 g of silver carbonate in the same manner as in Example 2, thereby obtaining 3.169 g of silver salt of bis[(2,2,2-trifluoroethoxy)sulfonyl]amine, AgN(SO$_2$OCH$_2$CF$_3$)$_2$. The yield was 95%.

EXAMPLE 12

In this example, 2.450 g of bis[(2,2,2-trifluoro-ethoxy)sulfonyl]amine obtained in Example 1 was reacted with 0.811 g of yttrium oxide in the same manner as in Example 2, thereby obtaining 2.835 g of yttrium salt of bis[(2,2,2-trifluoroethoxy) sulfonyl]amine, Y[N(SO$_2$OCH$_2$CF$_3$)$_2$]$_3$. The yield was 92%.

EXAMPLE 13

In this example, 3.400 g of bis[(2,2,3,3,3-pentafluoropropoxy)sulfonyl]amine obtained in Example 3 was reacted with 0.300 g of sodium oxide in the same manner as in Example 2, thereby obtaining 3.498 g of sodium salt of bis[(2,2,3,3,3-pentafluoropropoxy)sulfonyl]amine, NaN(SO$_2$OCH$_2$CF$_2$CF$_3$)$_2$. The yield was 98%.

EXAMPLE 14

In this example, 3.100 g of bis[(2,2,3,3,3-pentafluoropropoxy)sulfonyl]amine obtained in Example 3 was reacted with 0.296 g of basic magnesium carbonate in the same manner as in Example 2, thereby obtaining 3.019 g of magnesium salt of bis[(2,2,3,3,3-pentafluoropropoxy)sulfonyl]amine, Mg[N(SO$_2$OCH$_2$CF$_2$CF$_3$)$_2$]$_2$. The yield was 95%.

EXAMPLE 15

In this example, 2.400 g of bis[(2,2,3,3-tetrafluoropropoxy) sulfonyl]amine obtained in Example 7 was reacted with 0.241 g of zinc oxide in the same manner as in Example 2, thereby obtaining 2.355 g of zinc salt of bis[(2,2,3,3-tetrafluoropropoxy) sulfonyl]amine, Zn[N(SO$_2$OCH$_2$CF$_2$CF$_2$H)$_2$]$_2$. The yield was 91%.

EXAMPLE 16

In this example, 1.250 g of bis[(1,1,1,3,3,3-hexafluoro-2-propoxy)sulfonyl]amine obtained in Example 5 was reacted with 0.386 g of tetraethylammonium hydroxide in the same manner as in Example 2, thereby obtaining 1.525 g of tetraethylammonium salt of bis[(1,1,1,3,3,3-hexafluoro-2-propoxy)sulfonyl]amine, (C$_2$H$_5$)$_4$NN(SO$_2$OCH$_2$(CF$_3$)$_2$)$_2$. The yield was 96%.

EXAMPLE 17

In this example, 1.230 g of bis[(1,1,1,3,3,3-hexafluoro-2-propoxy)sulfonyl]amine obtained in Example 5 was reacted with 0.204 g of pyridine in the same manner as in Example 2, except that acetonitrile was used as solvent, thereby obtaining 1.305 g of pyridinium salt of bis[(1,1,1,3,3,3-hexafluoro-2-propoxy)sulfonyl]amine, C$_5$H$_5$NHN(SO$_2$OCH(CF$_3$)$_2$)$_2$. The yield was 91%.

EXAMPLE 18

In this example, 1.260 g of bis[(1,1,1,3,3,3hexafluoro-2-propoxy)sulfonyl]amine obtained in Example 5 was reacted with 0.267 g of triethylamine in the same manner as in Example 2, except that acetonitrile was used as solvent, thereby obtaining 1.497 g of triethylamine salt of bis[(1,1,1,3,3,3-hexafluoro-2-propoxy) sulfonyl]amine, (C$_2$H$_5$)$_3$NHN(SO$_2$OCH(CF$_3$)$_2$)$_2$. The yield was 98%.

What is claimed is:

1. A method of preparing a compound which is a first amine, said compound having a fluorocarbon sulfonic acid ester group and being represented by the formula $M[Rf^1OSO_2NSO_2ORf^2]_n$, said method comprising:

(a) reacting a bis(chlorosulfonyl)amine represented by the formula $HN(SO_2Cl)_2$ with at least one fluoroalcohol represented by the formula $Rf^3OH$, thereby resulting in said first amine, wherein $Rf^1$ and $Rf^2$ represent the same or different fluorine-containing monovalent organic groups each of which has from 2 to 18 carbon atoms, a straight chain portion, a branched-chain portion, and/or a ring chain portion, and an optional unsaturated bond and an optional oxygen atom;

$Rf^3$ represents the same or different groups which are identical with said $Rf^1$ and said $Rf^2$;

M represents a positive ion which has a valence and is hydrogen; and n represents an integer that is the same as said valence.

2. A method according to claim 1, wherein the step (a) is conducted at a temperature from about 0° C. to about 200° C.

3. A method according to claim 2, wherein said temperature is from 40° C. to 100° C.

4. A method according to claim 1, wherein the step (a) is conducted in a solvent which is at least one selected from the group consisting of halogenated hydrocarbons, hydrocarbons, ethers, and nitrites.

5. A method according to claim 1, wherein said fluoroalcohol is represented by the general formula of $RfCH_2OH$ or of $(Rf)_2CHOH$ where Rf represents a fluoroalkyl group having from 1 to 8 carbon atoms.

6. A method according to claim 5, wherein said fluoroalcohol is one selected from the group consisting of 2,2,2-trifluoroethanol, 2,2,3,3,3-pentafluoropropanol, 1,1,1,3,3,3-hexafluoro-2-propanol, and 2,2,3,3-tetrafluoropropanol.

7. A method of preparing a compound which is a first salt of a first amine, said compound having a fluorocarbon sulfonic acid ester group and being represented by the formula $M[Rf^1OSO_2NSO_2ORf^2]_n$, said method comprising:

(a) reacting a bis(chlorosulfonyl)amine represented by the formula $HN(SO_2Cl)_2$ with at least one fluoroalcohol represented by the formula $Rf^3OH$, thereby resulting in said first amine, wherein $Rf^1$ and $Rf^2$ represent the same or different fluorine-containing monovalent organic groups each of which has from 2 to 18 carbon atoms, a straight chain portion, a branched-chain portion, and or a ring chain portion, and an optional unsaturated bond and an optional oxygen atom;

$Rf^3$ represents the same or different groups which are identical with said $Rf^1$ and said $Rf^2$; and (b) reacting said first amine with a third compound, so as to prepare said first salt, said third compound comprising M, which represents a positive ion having a valence and is one selected from the group consisting of ammonia; quaternary ammonium compounds; and hydroxides, oxides, carbonates, halides, fluorides, chlorides, bromides, iodides, or acetates of an element selected from the group consisting of alkali metals, alkali earth metals, transition metals, rare earth elements, aluminum, gallium, iridium, thallium, tin, lead, arsenic, antimony, and bismuth;

wherein n represents an integer that is the same as said valence.

8. A method according to claim 7, wherein said quaternary ammonium compounds are derived from primary, secondary or tertiary amines; heterocyclic amines; or aromatic amines; or are quaternary ammonium halides or quaternary ammonium hydroxides.

9. A method according to claim 7, wherein said third compound is one selected from the group consisting of lithium carbonate, silver carbonate, yttrium oxide, sodium hydroxide, basic magnesium carbonate, zinc oxide, tetraethylammonium hydroxide, pyridine, and triethylamine.

* * * * *